: US 11,246,737 B2
(45) Date of Patent: Feb. 15, 2022

(54) SYSTEM FOR THE TREATMENT OF ERECTILE DYSFUNCTION

(71) Applicant: Maqsood Jafri, Glen Carbon, IL (US)

(72) Inventor: Maqsood Jafri, Glen Carbon, IL (US)

( * ) Notice: Subject to any disclaimer, the term of this patent is extended or adjusted under 35 U.S.C. 154(b) by 163 days.

(21) Appl. No.: 16/795,114

(22) Filed: Feb. 19, 2020

(65) Prior Publication Data

US 2020/0229961 A1 Jul. 23, 2020

Related U.S. Application Data

(60) Provisional application No. 62/794,688, filed on Jan. 20, 2019.

(51) Int. Cl.
*A61F 5/41* (2006.01)

(52) U.S. Cl.
CPC .......... *A61F 5/41* (2013.01); *A61F 2005/412* (2013.01); *A61F 2005/414* (2013.01); *A61F 2005/415* (2013.01)

(58) Field of Classification Search
CPC .................. A61F 5/41; A61F 2005/411; A61F 2005/412; A61F 2005/414; A61F 2005/415
See application file for complete search history.

(56) References Cited

U.S. PATENT DOCUMENTS

| | | |
|---|---|---|
| 4,539,980 A | 9/1985 | Chaney |
| 4,641,638 A * | 2/1987 | Perry .................. A61F 5/41 600/39 |
| 4,690,135 A | 9/1987 | Gerow |
| 4,741,329 A | 5/1988 | Marcune |
| 5,195,943 A | 3/1993 | Chaney |
| 5,234,401 A | 8/1993 | Yamanaka |
| 5,306,227 A | 4/1994 | Osbon et al. |
| 5,695,444 A | 12/1997 | Chaney |
| 5,779,621 A | 7/1998 | Chaney |
| 5,855,548 A | 1/1999 | Place |
| 5,873,813 A | 2/1999 | Weiss |
| 5,885,205 A | 3/1999 | Kassman |
| 5,997,470 A | 12/1999 | Coates |
| 6,015,379 A | 1/2000 | Sachse |

(Continued)

FOREIGN PATENT DOCUMENTS

| | | |
|---|---|---|
| CN | 2109827 U | 7/1992 |
| CN | 102319134 A | 1/2012 |

(Continued)

*Primary Examiner* — Samuel G Gilbert
(74) *Attorney, Agent, or Firm* — Williams Intellectual Property; Benjamin F. Williams

(57) ABSTRACT

A system for the treatment of erectile dysfunction includes a pubic pad devised to be worn upon the pubis of a user in conjunction with an inflatable constriction member. The pubic pad creates a mated, airtight seal with the mouth of a vacuum tube. The inflatable constriction member may be inflated via an air tube accommodated within a transverse duct in the pad. Inflation of the constriction member is therefore enabled while the vacuum is instated and after tumesecnce is induced, to sustain maximum engorgement before the vacuum is released. Once the ring is inflated, the vacuum may to be released, the pad removed, leaving the constriction ring in place upon the erect penis to sustain the erection during intercourse.

17 Claims, 4 Drawing Sheets

(56) References Cited

U.S. PATENT DOCUMENTS

| | | |
|---|---|---|
| 6,231,502 B1 | 5/2001 | McCarty |
| 6,277,063 B1 | 8/2001 | Altshuler |
| 6,319,194 B1 | 11/2001 | Wulf |
| 6,458,073 B1 * | 10/2002 | Bonthuys .................. A61F 5/41 600/38 |
| 6,569,083 B1 | 5/2003 | Kassman |
| 6,659,938 B1 | 12/2003 | Orlowski et al. |
| 6,705,987 B2 | 3/2004 | Anderson et al. |
| 6,926,666 B2 | 8/2005 | Magee |
| 7,261,685 B2 | 8/2007 | Wu |
| 7,341,553 B2 | 3/2008 | Egretier |
| 7,390,297 B2 | 6/2008 | Ford |
| 8,123,674 B2 | 2/2012 | Kuyava |
| 8,382,655 B2 | 2/2013 | Dela Cruz |
| 9,700,454 B2 | 7/2017 | Parlante |
| 2002/0033179 A1 | 3/2002 | Burgos |
| 2004/0094164 A1 | 5/2004 | Feingold et al. |
| 2006/0229494 A1 | 10/2006 | Wu |
| 2013/0237752 A1 * | 9/2013 | Suarez ..................... A61F 5/41 600/41 |
| 2014/0171734 A1 | 6/2014 | Kassman |
| 2019/0254862 A1 | 8/2019 | Tucker |

FOREIGN PATENT DOCUMENTS

| | | |
|---|---|---|
| DE | 102009030914 A1 | 12/2010 |
| EP | 0246520 A1 | 11/1987 |
| EP | 1539048 B1 | 2/2009 |
| WO | WO1990004368 A1 | 5/1990 |
| WO | WO9747260 A1 | 12/1997 |
| WO | WO2009129357 A2 | 10/2009 |

* cited by examiner

SYSTEM FOR THE TREATMENT OF ERECTILE DYSFUNCTION

BACKGROUND OF THE INVENTION

Characterized by the inability to achieve or sustain an erection, erectile dysfunction ("E.D.") is a physical condition that affects millions of men worldwide. It is estimated that approximately 5% of men over the age of 40 suffer from complete E.D. This figure increases threefold, to 15% of men at age 70.

Moderate E.D. affects approximately 10% of men per decade of life (e.g. approximately 50% of men in their 50s, 60% of men in their 60s, and so on).

Various devices have been devised to treat the symptoms of E.D. However, many are cumbersome, require invasive surgery, and fail to operate effectively to induce and sustain a natural erection to maintain tumescence and preserve the sensation and pleasure of sexual intercourse.

What is needed is a means of inducing an erection by application of a vacuum tube positioned in sealable engagement with a wearable pubic pad which enables inflation of a constriction member to sustain the erection induced.

FIELD OF THE INVENTION

The present invention relates to a system for the treatment of erectile dysfunction that includes a pubic pad wearable in conjunction with an inflatable constriction member. The pubic pad is devised for sealable engagement with a vacuum tube mouth to enable creation of a stronger vacuum. An inflatable constriction member is wearable in conjunction with the pubic pad for inflation after the erection is induced. Outflow of blood from the penis is therefore constricted before the vacuum is released enabling a user to sustain tumescence at a maximized engorgement of penile tissue.

SUMMARY OF THE INVENTION

The present system for the treatment of erectile dysfunction has been devised to enable inducement of an erection by application of a vacuum tube to a user's penis. Once induced, the erection is sustained by a constriction member that is inflated before the vacuum is released and the vacuum tube removed.

A pubic pad is configured to effectively seal the vacuum tube overtop the penis, to increase the efficacy of the vacuum applied to the penis when inducing the erection. The pubic pad also accommodates inflation of an inflatable constriction ring installed around the penis to constrict outflow of blood from the penis and sustain the erection once attained.

The pubic pad is worn upon the pubis of the user, encircling the user's penis. The pubic pad includes an obverse surface configured to form an airtight seal against the mouth of the vacuum tube and a reverse surface disposed to seal against the pubis of the user. The evacuation of the vacuum tube is therefore more properly effective, since the vacuum is not interrupted by imposition of ambient air escaping into the vacuum through an imperfect seal as may otherwise result in use of the vacuum tube directly against the user's body in the absence of the pubic pad. Application of a relatively stronger vacuum (herein also termed a "strong vacuum") is therefore possible.

The vacuum attained is contemplated to be sufficient to draw blood flow into the penis and induce an erection into the evacuated space delimited within the vacuum tube. Once the erection is induced, a constriction member that is worn in conjunction with the pubic pad may be inflated to constrict outflow of blood from the user's penis before the vacuum is released. Once the constriction member is inflated, then, the vacuum may be released and the vacuum tube and pubic pad removed, leaving only the constriction ring in place to constrict outflow of blood from the penis and maintain tumescence. The constriction of the user's penis is therefore applicable while the vacuum is instated, at a maximal engorgement of the penis.

The pubic pad is contemplated to be an elastomeric, flexible, rubberlike, or polymeric body having an aperture disposed therein. The pad is fittable over the unerect penis of a user and positioned at the base of the penis, upon the pubis of the user. The pad includes an outer edge, bounding the pubic pad; an inner edge, circumferentially or perimetrically bounding the aperture; an obverse surface configured to form an airtight seal with the mouth of the vacuum tube; and a reverse surface, configured for contact with the user's body and pubic region. A bushing, flanged, or other raised annular member may be disposed on the reverse surface to assist in making sealable contact against the body of a user. In various embodiments, the pubic pad may cover a greater or lesser area but is devised for sealable contact against the body of a user and to present the obverse surface for sealable contact with the vacuum tube. The pad may therefore be annular with a diameter approximate to that of the vacuum tube.

A transverse duct is disposed through the pubic pad, or accommodated under the obverse surface, from the outer edge to the inner edge of the pad, to accommodate passage of an air tube into the aperture. The air tube is devised for interconnection with at least one valve disposed upon the inflatable constriction member, and patency of the tube is maintained by accommodation of the tube within the transverse duct. Therefore, the constriction member may, in multiple embodiments, be interconnected with an air pump for selective inflation without removing the vacuum tube or breaking the airtight seal achieved when the vacuum is instated to induce the erection. Thus, constriction of the penis is enabled once maximized engorgement has been attained via application of the strong vacuum.

In one embodiment contemplated herein, the constriction member includes at least one ring. The ring is contemplated to be an elastomeric, inflatable ring that is configured to fit nested within the aperture of the pubic pad, encircling the base of the user's penis. The diameter of the ring is contemplated to be less than the diameter of the aperture. The ring may be connected to a manual, handheld, or other air pump via the tube that is accommodated through the transverse duct disposed in the pubic pad. The tube is accommodated through the transverse duct to provide an airtight seal between the tube and the duct, while ensuring that patency of the tube is maintained. In some embodiments contemplated as part of this disclosure, the at least one ring may be hoop-shaped, enabling application of the ring directly at the base of the user's unerect penis without having to insert the penis through the ring. In such embodiments, the hoop-shaped ring may rigidify at pressure when inflated to maintain a first end and a second end unconnected. Alternatively, the first end and the second end may be interconnectable by mating engagement when inflated or deflated, or by action of a buckle, sleeve, or other connecting member that supports and connects the first and second ends together.

At least one embodiment of the constriction member further contemplates a pair of rings disposed at each end of at least one inflatable splint member to enable constriction of blood approximal the glans as well as at the base of the penis. In this embodiment, a proximal ring is positioned at the base of the user's penis and a distal ring is positioned approximal the glans of the user's penis. At least one inflatable splint is disposed connecting the proximal and distal rings, to enable airflow therebetween as well as to provide structural support in lengthening the penis during tumescence. (In some embodiments contemplated herein, at least one splint may be non-inflatable.) The pad is positionable surrounding the proximal ring, in the manner already described. The proximal ring is thence connectable with the air tube for selective inflation of the constriction member once tumescence has already been attained and without releasing the vacuum applied. In this particular embodiment, pressurization of the constriction member occurs via the proximal ring, the inflatable splint (which communicates airflow through to the distal ring) and the distal ring together. Lengthening of the user's penis is attained as the inflatable splint rigidifies at pressure, and constriction is applied at the base of the user's penis and also approximal the glans to maintain engorgement of the user's penis and sustain maximized tumescence.

In this embodiment, also, the pair of rings may be open-ended for easier and direct application to the user's penis. This enables direct fit of each ring in place, without the user having to first position the penis through the rings. In this embodiment, the means of connecting the ends of the rings together is preferable to maintain the position of at least the distal ring in its desired location upon the unerect penis. Thus, in this embodiment particularly, a means of connecting the ends of at least the distal ring is contemplated as within the scope of the disclosure. Such means of connecting the first and second ends of each ring, applicable to all embodiments contemplated herein, may include for example interlocking complementary shapes, a buckle, a tie, action of an elastomeric sleeve member extensible from one end to engage with the other, or by other mating or interlocking engagement or interconnection, tie, hook, hasp, lock, or other such means of interconnection known in the art.

At least one embodiment of the pubic pad includes a recessed annular surface disposed in the reverse surface of the pad, surrounding the aperture. This recessed annular surface is devised to create a space between the obverse surface of the pad and the body of the user whereby the obverse surface essentially overhangs the aperture. The recessed annular surface thereby enables accommodation of additional objects connected to the constriction member, such as, for example, vibratory units, or other stimulating devices as may be additional to the constriction member as worn at the base of the penis.

Thus, has been broadly outlined the more important features of the present system for the treatment of erectile dysfunction so that the detailed description thereof that follows may be better understood and in order that the present contribution to the art may be better appreciated.

Objects of the present system for the treatment of erectile dysfunction, along with various novel features that characterize the invention, are particularly pointed out in the claims forming a part of this disclosure. For a better understanding of the system for the treatment of erectile dysfunction, its operating advantages and specific objects attained by its uses, refer to the accompanying drawings and description.

BRIEF DESCRIPTION OF THE DRAWINGS

Figures

DETAILED DESCRIPTION OF THE DRAWINGS

With reference now to the drawings, and in particular FIGS. 1 through 12 thereof, example of the instant system for the treatment of erectile dysfunction employing the principles and concepts of the present system for the treatment of erectile dysfunction and generally designated by the reference number 10 will be described.

Referring to FIGS. 1 through 12 example embodiments of the present system for the treatment of erectile dysfunction 10 are illustrated.

Figure 1:
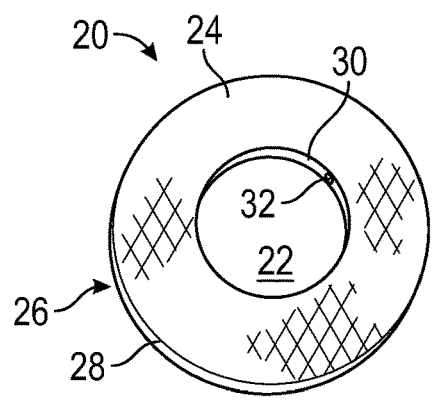
FIG. 1 is a top elevation view of an example embodiment of a pubic pad.

FIG. 1 shows a top elevation view of an example embodiment of a pubic pad 20 wearable by a user. In the example embodiment depicted, the pubic pad 20 is devised annularly, however differing shapes are contemplated as within scope of the invention where not departing from the general motivation and performance intended.

The user's penis 100 is placed through aperture 22 so that the pubic pad 20 circumferentially bounds the base of the user's penis 100. Pubic pad 20 is generally positioned upon the pubis of the user to gird the base of the penis 100 (see for example FIG. 3). Pubic pad 20 includes obverse surface 24, reverse surface 26, outer edge 28, and inner edge 30. Transverse duct 32 is disposed from outer edge 28 to inner edge 30 to enable passage (and maintain patency of) air tube 80 (see for example FIG. 2) and, alternatively, airflow (see for example FIG. 13). A bushing, flange, or other annular member (not shown) may be disposed upon the reverse surface 26 to assist in forming sealable contact against the body of the user.

Figure 2:
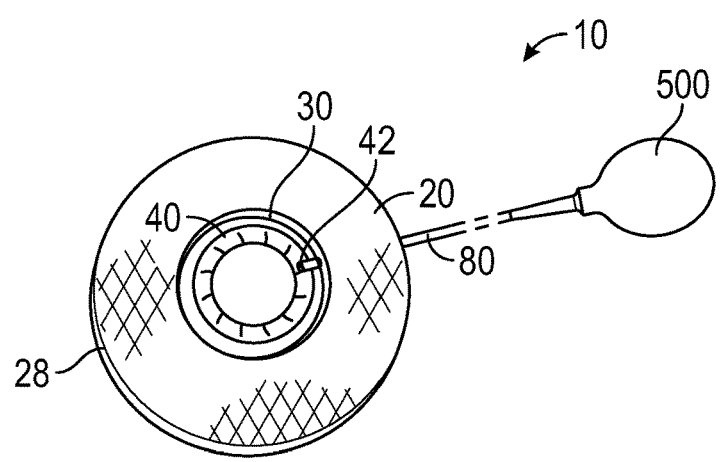
FIG. 2 is a top elevation view of an example embodiment of the pubic pad in conjunction with an inflatable constriction member having at least one inflatable ring connected with a manual pump.

FIG. 2 illustrates the pubic pad 20 disposed in conjunction with an inflatable constriction member 40. In this example embodiment shown, constriction member 40 is a ring. Constriction member 40 includes at least one valve 42, connectable to air tube 80, for operational communication with air pump 500. In the example embodiment depicted, air pump 500 is a handheld, stylized pump, however additional pumps are contemplated as within scope of this invention including, for example, electric pumps, or even pumps operatively coupled with the vacuum tube proper. Constriction member 40 may include a separate pressure release valve (not shown) for manual deflation of the ring. Alternatively, valve 42 may accommodate deflation by manual engagement thereof, or by manual action effected at the pump 500 interconnected therewith, which may control airflow into and out of the constriction member 40, as case may be. Operative coupling of a pressure gauge (not shown) in operational communication with valve 42, to ascertain internal pressure within the constriction member, is also contemplated for use in some embodiments.

Figure 3:
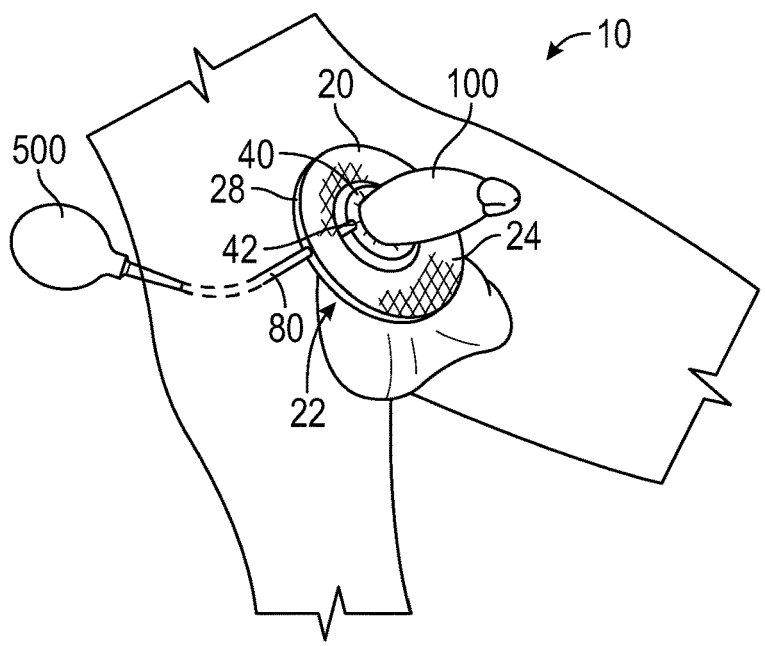
FIG. 3 is an elevation view of an example embodiment of the pubic pad in-use, worn by the user in conjunction with the inflatable constriction member.

As show in FIG. 3, constriction member 40 and pubic pad 20 are worn in conjunction by a user. Constriction member 40 is nested within aperture 22 of pubic pad 20. Obverse surface 24 is devised to provide sealable contact with rim 72 of vacuum tube 70 and may be rendered of any suitable material effective of the same. Example materials contemplated as within scope of this invention, but not intended to be limiting of the same, include silicone, rubber, polymer, elastomer, resin, plastic, or any other rubberlike, polymeric, or elastomeric substance(s) known to sealably contact with a glass, plastic, or polymeric rim of vacuum tube 70.

Figure 4:
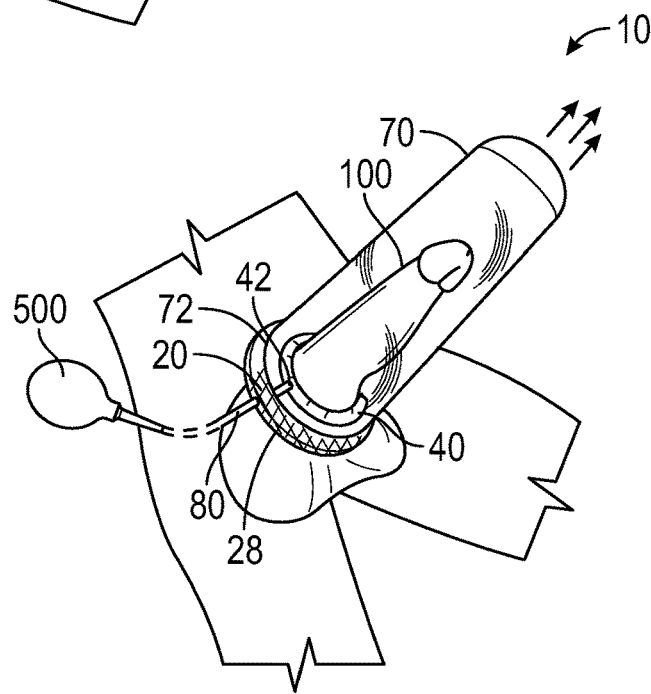
FIG. 4 is an elevation view of an example embodiment of the pubic pad in-use with a vacuum tube applied atop an obverse surface of the pad to induce tumescence.
Figure 5:
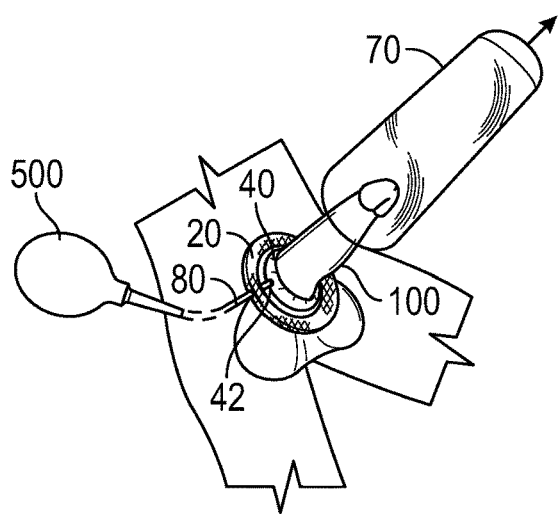
FIG. 5 is an elevation view of an example embodiment after the constriction member has been inflated and the vacuum released for removal of the vacuum tube.
Figure 6:
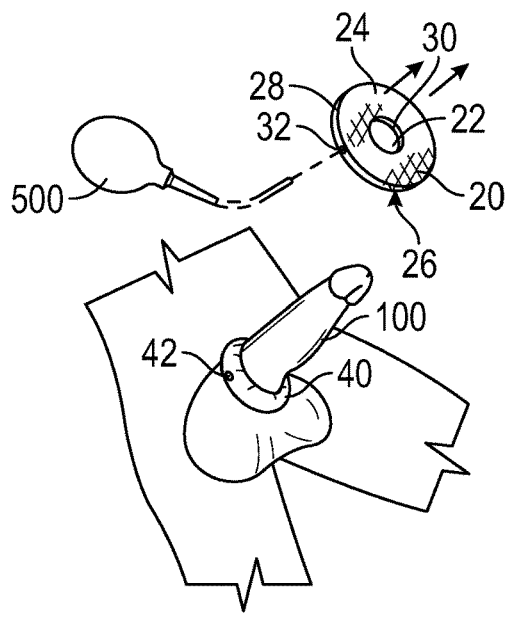
FIG. 6 is an elevation view of an example embodiment after removal of the pubic pad and disconnection of the air pump.

As shown in FIG. 4, vacuum tube 70 is positionable to contact obverse surface 24 to create an airtight seal with the vacuum tube 70. A vacuum is thence applied to induce tumescence and engorge the penis. Once the vacuum is instated, and tumescence attained, the user may inflate constriction member 40 by action of the interconnected pump 500 to constrict the penis before the vacuum is released. Once constriction member 40 is inflated to a desired pressure, the vacuum may be released and the vacuum tube 70 removed. See for example FIG. 5. Air tube 80 is thence disconnectable from the constriction member 40, pubic pad 20 is removable, and the user's penis is exposed with just constriction member 40 in place. See for example FIG. 6.

Figure 7:
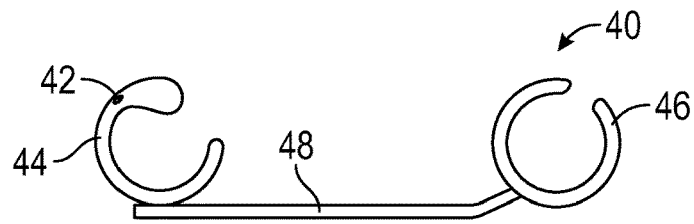
FIG. 7 is an elevation view of an example embodiment of the inflatable constriction member having a proximal ring and a distal ring interconnected by an inflatable splint.
Figure 8:
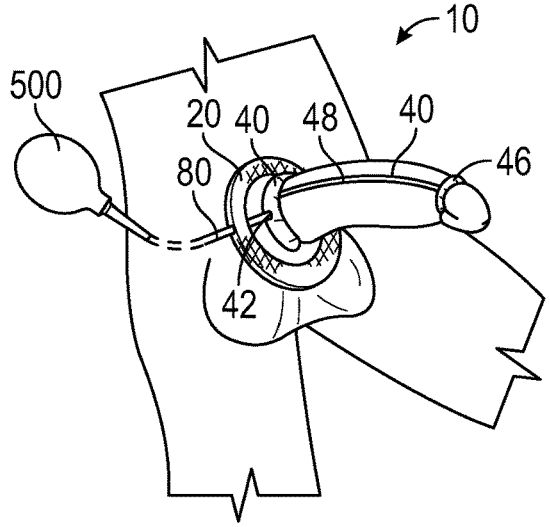
FIG. 8 is an in-use elevation view of the example embodiment of FIG. 7 worn in conjunction with the pubic pad.
Figure 9:
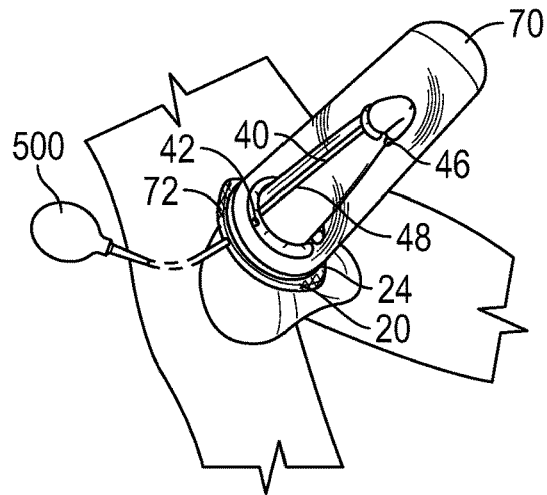
FIG. 9 is an in-use elevation view of the example embodiment of FIG. 8 showing application of the vacuum tube to induce tumescence.
Figure 10:
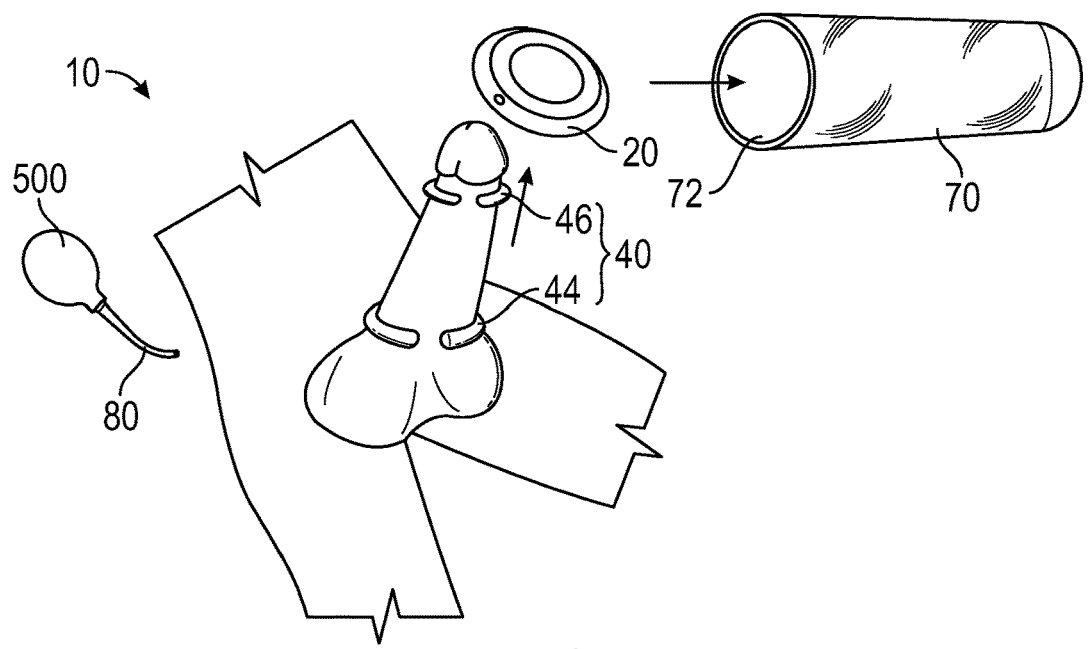
FIG. 10 is an in-use elevation view of the example embodiment of FIG. 9 after inflation of the constriction member and removal of the vacuum tube and pubic pad.

FIG. 7 illustrates an example embodiment of an inflatable constriction member 40. In this particular embodiment, constriction member 40 includes proximal ring 44, distal ring 46, and inflatable splint 48. Proximal ring 44 is configured for use in a manner generally consistent with the examples already discussed and illustrated above, worn at the base of the penis 100 and inflatable by nesting interior to the aperture 22 of the pubic pad 20 after the vacuum has been instated and the erection attained (see for example FIG. 9). Distal ring 46 is included for installation approximal the glans of a user, to constrict outflow of blood from the glans. As shown in FIG. 8, constriction member 40 is fitted to the user's penis 100 in conjunction with pubic pad 20. Proximal ring 44 is then connected to air tube 80 at valve 42, as in the previous embodiment disclosed. As shown in FIG. 9, once an erection is induced, constriction member 40 may be inflated by action of air pump 500 to rigidify the proximal ring 44, the inflatable splint 48, and the distal ring 46, assist in lengthening the penis 100 during tumescence and constrict the penis 100 at the base and approximal the glans when a maximized tumescence has been induced by application of the strong vacuum. In like manner as previously described, once constriction member 40 has been inflated to a desired pressure, the vacuum may be released and the vacuum tube 70 and pad 20 removed. See for example FIG. 10.

Figure 12:
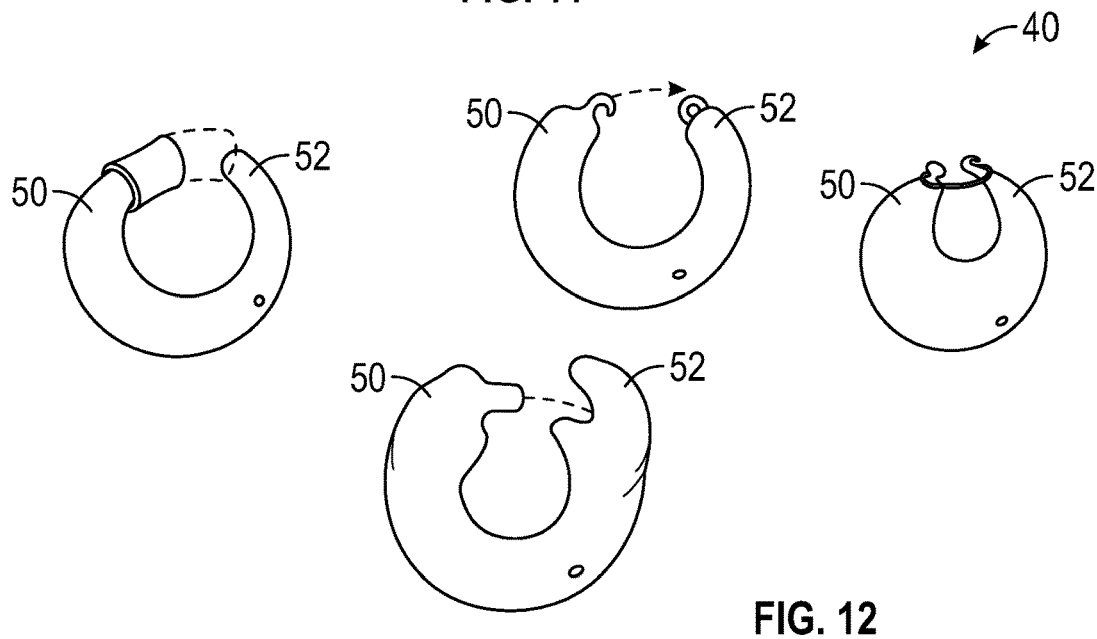
FIG. 12 is an elevation view of an example embodiment of a constriction member having a hoop-shaped ring with connectable ends.

In the example embodiment depicted in FIG. 7, the proximal ring 44 and distal ring 46 are hoop-shaped and open-ended. Each ring 44, 46 therefore includes a first end 50 and a second end 52 that may be connectable together (see for example FIG. 12). In such an embodiment, the constriction member 40 is more easily fitted to the unerect penis. Proximal and distal rings 44, 46 may be attached directly to the penis 100 without the user having to first position the unerect penis 100 through the rings 44, 46. It should be understood that such a hoop-shaped embodiment is contemplated in practice of any ring as may be employed in enabling the constriction member 40 as devised in the present invention 10. In such an embodiment, ends 50, 52 may be connectable together (see for example FIG. 12) or may remain disconnected. Where ends 50, 52 of the ring remain disconnected, the ring may rigidify at pressure and be positionable such that the gap between the ends 50, 52 is situated to accommodate the user's urethra. This may be preferable for enablement of the distal ring 46. However, connection of ends 50, 52 of the ring is also contemplated as within scope of this disclosure, whereby an elastomeric sleeve member 82 may extend from the second end 52 to connect with the first end 50, for example. Additional means of effectuating the connection are contemplated as within the scope of this disclosure, including a tie, a buckle, a hasp, a clip, a belt, a hook and loop portion, or interconnecting members devised to connect together at each of the first and second end, an optionally connectable tie or body or connection means that may be applicable to the ends 50, 52 to draw them together, among other means known in the art. Such interconnection enables securement of the constriction member 40 to the unerect penis at a desired position before and during the application of the vacuum, such as approximal the glans. Nonlimiting examples are shown in FIG. 12.

Figure 11:
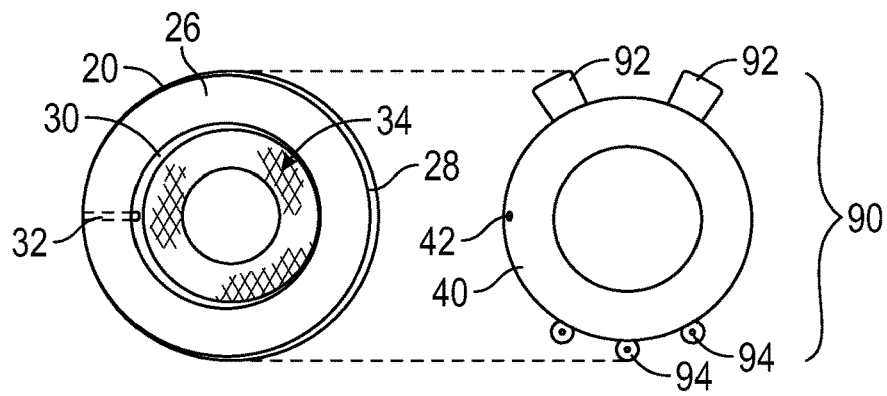
FIG. 11 is an elevation view of an example embodiment of the pubic pad having a recessed annular surface in the reverse side for accommodation of a constriction member having additional elements, such as vibratory units, attached.

FIG. 11 depicts an example embodiment of pubic pad 20 having a recessed annular surface 34 disposed in the reverse surface 26 encircling (or, in other potential embodiments, bounding) aperture 22. This recessed annular surface 34 is incorporated to accommodate additional elements 90 as may be used attached to or used in conjunction with constriction member 40, such as vibratory units 92 or stimulation beads 94. In such an embodiment, the obverse surface 24 effectively overhangs aperture 22, whereby the airtight seal with the vacuum tube 70 mouth is enabled and the additional elements 90 are accommodated under the obverse surface 24 in the space above the recessed annular surface 34.

Figure 13:
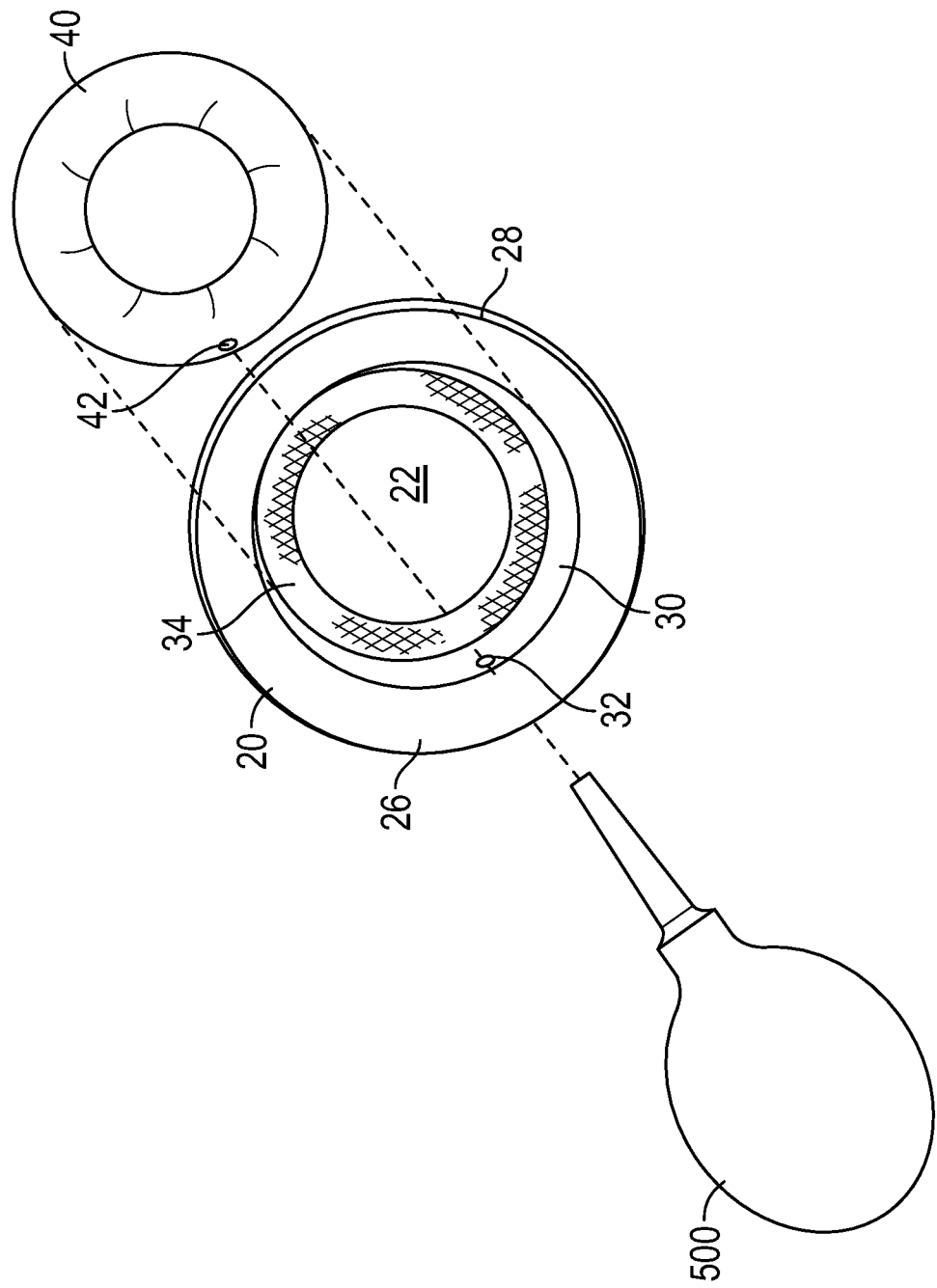
FIG. 13 is an elevation view of an example embodiment of the pubic pad illustrating in FIG. 11 that operatively couples with an example embodiment of the constriction member fit into the recessed annular surface.

FIG. 13 depicts an alternative embodiment of pubic pad 20 and inflatable constriction member 40. In this embodiment, constriction member 40 seats into recessed annular surface 34 disposed in reverse side 26 of pad 20. Such an arrangement may enable accommodation of constriction member 40 at least partially under obverse surface 24 and therefore creation of a stronger vacuum. Further, in this example embodiment, operative coupling of constriction member 40 to pubic pad 20 is contemplated, whereby valve 42 may be caused to engage with the transverse duct 32 at inner edge 30. Coupling of air pump 500 to the pad 20 at the outer edge 28 may thence enable easier inflation of the inflatable constriction member 40 once the erection has been attained. Decoupling of the pump 500 may be more readily effected, and removal of the pad 20 may disengage operative coupling with the constriction member 40 whereby the valve 42 maintains pressure interior to the constriction member 40.

What is claimed is:

1. A system for the treatment of erectile dysfunction comprising:
    a pubic pad configured to gird a user's penis, said pad having:
        an aperture;
        an inner edge;
        an obverse surface configured to sealably contact the rim of a vacuum tube; and
        a reverse surface configured to sealably contact the user's body when applying a vacuum to induce an erection;
    an inflatable constriction member wearable upon the user's penis in conjunction with the pubic pad nested within the aperture of the pubic pad, said inflatable constriction member having a valve connectable to an air tube accommodated under or through the pubic pad;
    wherein an airtight seal is formable around a rim of the vacuum tube when placed in contact with the pubic pad to increase a relative strength of the vacuum applied to the penis wherein the inflatable constriction member is inflatable after an erection has been induced to constrict blood flow out of the penis before the vacuum has been released and wherein the pubic pad is removable leaving only the constriction member girding the user's penis.

2. The system for the treatment of erectile dysfunction of claim 1 wherein the inflatable constriction member comprises at least one ring.

3. The system for the treatment of erectile dysfunction of claim 2 wherein the at least one ring comprises:
    a first end and a second end unconnected to the first end;
    wherein the at least one ring is hoop-shaped and the said ring may be opened for direct application to the user's penis before the said ring is inflated and whereby inflation of the said ring rigidifies the ring in position about the user's penis.

4. The system for the treatment of erectile dysfunction of claim 3 wherein the first end and the second end include connection means by which said first and second end are connectable together.

5. The system for the treatment of erectile dysfunction of claim 2 where the inflatable constriction member comprises a proximal ring and a distal ring interconnected by an inflatable splint.

6. The system for the treatment of erectile dysfunction of claim 5 wherein the proximal ring and the distal ring each comprise:
    a first end; and
    a second end unconnected from the first end;
    wherein the first and second ring are hoop-shaped and each said ring may be opened for direct application to portions of the user's penis before they are inflated whereby inflation of each said ring rigidifies the said rings in position about the user's penis.

7. The system for the treatment of erectile dysfunction of claim 1 wherein the pubic pad comprises a recessed annular surface disposed in the reverse surface, said recessed annular surface disposed to enable accommodation of the inflatable constriction member therein.

8. The system for the treatment of erectile dysfunction of claim 7 wherein the recessed annular surface is devised to accommodate at least one additional element usable upon or in connection with the inflatable constriction ring.

9. A system for the treatment of erectile dysfunction comprising:
    a pubic pad configured to gird a user's penis, said pubic pad comprising:
        an elastomeric body having an outer edge and an inner edge disposed circumferentially or perimetrically bounding an aperture;
        an obverse surface configured to sealably engage with a rim of a vacuum tube to create an airtight seal when the rim is contacted thereagainst;
        a reverse surface configured to sealably contact the user;
        a transverse duct disposed from the outer edge of the pubic pad through to the inner edge, said transverse duct configured to accommodate passage of an air tube therethrough; and
    an elastomeric, inflatable constriction member having a diameter generally less than a diameter of the aperture of the pubic pad, said constriction member comprising:
        an air valve alignable with the transverse duct for interconnection with the air tube;
    wherein the pubic pad is wearable in conjunction with the constriction member nested in the aperture; and
    wherein the constriction member is inflatable after an erection has been induced into the vacuum tube, while a vacuum is instated and before the vacuum is released and wherein the pubic pad is removable leaving only the constriction member in place girding the user's penis.

10. The system for the treatment of erectile dysfunction of claim 9 wherein the inflatable constriction member comprises at least one ring.

11. The system for the treatment of erectile dysfunction of claim 10 wherein the at least one ring comprises:
    a first end and a second end unconnected to the first end;
    wherein the at least one ring is hoop-shaped and the said ring may be opened for direct application to the user's penis before the said ring is inflated and whereby inflation of the said ring rigidifies the ring in position about the user's penis.

12. The at least one ring of claim 11 wherein the first end and the second end include connection means whereby the first and the second end are connectable together.

13. The system for the treatment of erectile dysfunction of claim 10 where the inflatable constriction member comprises a proximal ring and a distal ring interconnected by an inflatable splint.

14. The system for the treatment of erectile dysfunction of claim 13 wherein the proximal ring and the distal ring each comprise:
    a first end; and
    a second end unconnected from the first end;
    wherein the first and second ring are hoop-shaped and each said ring may be opened for direct application to portions of the user's penis before they are inflated whereby inflation of each said ring rigidifies the said rings in position about the user's penis.

15. The system for the treatment of erectile dysfunction of claim 9 wherein the pubic pad comprises a recessed annular surface disposed in the reverse surface, said recessed annular surface disposed to enable accommodation of the inflatable constriction member therein.

16. The system for the treatment of erectile dysfunction of claim 15 wherein the recessed annular surface is devised to accommodate an additional element disposed upon or used in conjunction with the inflatable constriction ring.

17. The system for the treatment of erectile dysfunction of claim 15 wherein the transverse channel is configured to be connected to an air pump at the outer edge of the pubic pad and the constriction member seats into the recessed annular surface such that the valve mates with the transverse channel at the inner edge.

\* \* \* \* \*